(12) United States Patent  
Baril et al.

(10) Patent No.: US 10,548,602 B2  
(45) Date of Patent: Feb. 4, 2020

(54) ENDOSCOPIC SURGICAL CLIP APPLIER

(71) Applicant: Covidien LP, Mansfield, MA (US)

(72) Inventors: Jacob Baril, White Plains, NY (US); Brian Creston, West Haven, CT (US); Justin Williams, Southbury, CT (US); Thomas Zammataro, Hamden, CT (US)

(73) Assignee: Covidien LP, Mansfield, MA (US)

( * ) Notice: Subject to any disclaimer, the term of this patent is extended or adjusted under 35 U.S.C. 154(b) by 205 days.

(21) Appl. No.: 15/863,763

(22) Filed: Jan. 5, 2018

(65) Prior Publication Data

US 2018/0235633 A1    Aug. 23, 2018

Related U.S. Application Data

(60) Provisional application No. 62/462,407, filed on Feb. 23, 2017.

(51) Int. Cl.
    *A61B 17/10*      (2006.01)
    *A61B 17/00*      (2006.01)

(52) U.S. Cl.
    CPC ............ *A61B 17/105* (2013.01); *A61B 17/10* (2013.01); *A61B 2017/0046* (2013.01); *A61B 2017/00407* (2013.01)

(58) Field of Classification Search
    CPC .............................. A61B 17/10; A61B 17/105
    See application file for complete search history.

(56) References Cited

U.S. PATENT DOCUMENTS

| | | |
|---|---|---|
| 3,120,230 A | 2/1964 | Skold |
| 3,363,628 A | 1/1968 | Wood |
| 3,638,847 A | 2/1972 | Noiles et al. |
| 3,675,688 A | 7/1972 | Bryan et al. |
| 3,735,762 A | 5/1973 | Bryan et al. |

(Continued)

FOREIGN PATENT DOCUMENTS

| | | |
|---|---|---|
| AU | 2013254887 A1 | 11/2013 |
| CA | 1163889 A | 3/1984 |

(Continued)

OTHER PUBLICATIONS

European Office Action corresponding to European Appln. No. EP 16 15 9324.9 dated Aug. 7, 2017.

(Continued)

*Primary Examiner* — Richard G Louis

(57) ABSTRACT

An endoscopic surgical clip applier includes an endoscopic assembly and a handle assembly. The handle assembly includes a housing, a trigger, a drive bar, and a ratchet assembly. The ratchet assembly includes a first rack, a second rack, a pawl housing engageable with the first rack, and a second pawl engageable with the second rack. In a first position, the pawl housing is in registration with the first rack to prohibit reversal of a direction of movement of the trigger until the pawl housing is disposed beyond a proximal end or a distal end of the first rack. In a second position, the pawl housing is out of registration with the first rack to permit reversal of the movement of the trigger after the second pawl is disposed distally beyond a distal end of the second rack or proximally beyond a proximal end of the second rack.

20 Claims, 9 Drawing Sheets

(56) References Cited

U.S. PATENT DOCUMENTS

| | | |
|---|---|---|
| 3,867,944 A | 2/1975 | Samuels |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |
| 4,471,780 A | 9/1984 | Menges et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |

(56) References Cited

U.S. PATENT DOCUMENTS

| | | |
|---|---|---|
| 5,441,509 A | 8/1995 | Vidal et al. |
| 5,447,513 A | 9/1995 | Davison et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sheds et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |

(56) References Cited

U.S. PATENT DOCUMENTS

| | | |
|---|---|---|
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B1 | 5/2005 | McClellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns |
| 7,488,335 B2 | 2/2009 | Sgro |
| 7,510,562 B2 | 3/2009 | Lindsay |
| 7,552,853 B2 | 6/2009 | Mas et al. |
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |

(56) References Cited

U.S. PATENT DOCUMENTS

| | | |
|---|---|---|
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,887,553 B2 | 2/2011 | Lehman et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,890 B2 | 5/2011 | D'Agostino et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huiterna et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huitema |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,931 B2 | 12/2014 | Boudreaux et al. |
| 8,939,974 B2 | 1/2015 | Boudreaux et al. |
| 8,945,151 B2 | 2/2015 | Salas |
| 8,950,646 B2 | 2/2015 | Viola |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |

(56) References Cited

U.S. PATENT DOCUMENTS

| | | |
|---|---|---|
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,439,654 B2 | 9/2016 | Sorrentino et al. |
| 9,445,820 B2 | 9/2016 | Whiting |
| 9,468,444 B2 | 10/2016 | Menn et al. |
| 9,480,477 B2 | 11/2016 | Aranyi et al. |
| 9,480,480 B2 | 11/2016 | Santini et al. |
| 9,486,225 B2 | 11/2016 | Michler et al. |
| 9,498,227 B2 | 11/2016 | Zergiebel et al. |
| 9,517,064 B2 | 12/2016 | Sarradon |
| 9,526,501 B2 | 12/2016 | Malkowski |
| 9,545,254 B2 | 1/2017 | Sorrentino et al. |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,687,247 B2 | 6/2017 | Aranyi et al. |
| 9,717,505 B2 | 8/2017 | Whitfield et al. |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,775,623 B2 | 10/2017 | Zammataro et al. |
| 9,775,624 B2 | 10/2017 | Rockrohr et al. |
| 9,848,886 B2 | 12/2017 | Malkowski et al. |
| 9,855,043 B2 | 1/2018 | Malkowski |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0010242 A1 | 1/2005 | Lindsay |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020271 A1 | 1/2006 | Stewart et al. |
| 2006/0085015 A1 | 4/2006 | Whitfield et al. |
| 2006/0100649 A1 | 5/2006 | Hart |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235439 A1 | 10/2006 | Molitor et al. |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | A. Morris |
| 2007/0093790 A1 | 4/2007 | Downey et al. |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0045981 A1 | 2/2008 | Margolin et al. |
| 2008/0051808 A1 | 2/2008 | Rivera et al. |
| 2008/0083806 A1* | 4/2008 | Scirica ............... A61B 17/0686 227/175.1 |
| 2008/0103510 A1 | 5/2008 | Taylor et al. |
| 2008/0147092 A1 | 6/2008 | Rogge et al. |
| 2008/0167665 A1 | 7/2008 | Arp et al. |
| 2008/0210738 A1* | 9/2008 | Shelton ............... A61B 17/064 227/176.1 |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312670 A1 | 12/2008 | Lutze et al. |
| 2009/0088783 A1 | 4/2009 | Kennedy et al. |
| 2009/0182193 A1 | 7/2009 | Whitman et al. |
| 2009/0209946 A1 | 8/2009 | Swayze et al. |
| 2009/0228023 A1 | 9/2009 | Cui |
| 2009/0326558 A1 | 12/2009 | Cui et al. |
| 2010/0274264 A1 | 10/2010 | Schulz et al. |
| 2010/0318103 A1 | 12/2010 | Cheng et al. |
| 2011/0054498 A1 | 3/2011 | Monassevitch et al. |
| 2011/0144662 A1 | 6/2011 | McLawhorn et al. |
| 2011/0208211 A1 | 8/2011 | Whitfield et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0295290 A1 | 12/2011 | Whitfield |
| 2011/0313437 A1 | 12/2011 | Yeh |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0226291 A1 | 9/2012 | Malizia et al. |
| 2012/0253298 A1 | 10/2012 | Henderson et al. |

(56) References Cited

U.S. PATENT DOCUMENTS

| | | |
|---|---|---|
| 2012/0265220 A1 | 10/2012 | Menn |
| 2012/0330326 A1 | 12/2012 | Creston et al. |
| 2013/0131697 A1 | 5/2013 | Hartoumbekis |
| 2013/0165951 A1 | 6/2013 | Blake, III |
| 2013/0172909 A1 | 7/2013 | Harris |
| 2013/0172910 A1 | 7/2013 | Malkowski |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2014/0074143 A1 | 3/2014 | Fitzgerald et al. |
| 2014/0263565 A1 | 9/2014 | Lytle, IV et al. |
| 2014/0276970 A1 | 9/2014 | Messerly et al. |
| 2015/0032131 A1 | 1/2015 | Sorrentino et al. |
| 2015/0045816 A1 | 2/2015 | Aranyi et al. |
| 2015/0351771 A1 | 12/2015 | Malkowski et al. |
| 2015/0351772 A1 | 12/2015 | Malkowski et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0242767 A1 | 8/2016 | Kasvikis |
| 2016/0262764 A1 | 9/2016 | Gokharu |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Murthy Aravalli |
| 2017/0238936 A1 | 8/2017 | Mujawar |
| 2017/0258472 A1 | 9/2017 | Aranyi et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |

FOREIGN PATENT DOCUMENTS

| | | |
|---|---|---|
| CN | 104605911 B | 2/2017 |
| DE | 202005001664 U1 | 5/2005 |
| DE | 202007003398 U1 | 6/2007 |
| DE | 202009006113 U1 | 7/2009 |
| EP | 0000756 A1 | 2/1979 |
| EP | 0 406 724 A1 | 1/1991 |
| EP | 0514139 A2 | 11/1992 |
| EP | 0514139 A3 | 3/1993 |
| EP | 0 732 078 A2 | 9/1996 |
| EP | 1769757 A1 | 4/2007 |
| GB | 2073022 A | 10/1981 |
| JP | 2003-033361 A | 2/2003 |
| JP | 2006-154230 A | 6/2006 |
| JP | 2006-277221 A | 10/2006 |
| JP | 2008-017876 A | 1/2008 |
| WO | 0042922 A1 | 7/2000 |
| WO | 2001-66001 A2 | 9/2001 |
| WO | 2001-67965 A1 | 9/2001 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |

OTHER PUBLICATIONS

Chinese First Office Action corresponding to Chinese Appln. No. CN 2014104295806 dated Aug. 31, 2017.
Extended European Search Report corresponding to European Appln. No. EP 17 17 3508.7 dated Sep. 29, 2017.
Chinese Second Office Action corresponding to Chinese Appln. No. CN 201410076318.8 dated Oct. 10, 2017.
Extended European Search Report corresponding to European Appln. No. EP 17 18 0570.8 dated Dec. 6, 2017.
Extended European Search Report corresponding to Patent Application EP 18154617.7 dated Jun. 25, 2018.
Extended European Search Report corresponding to Patent Application EP 18155158.1 dated Jun. 28, 2018.
Extended European Search Report corresponding to Patent Application EP 15877428.1 dated Jul. 2, 2018.
Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extended European Search Report corresponding to Patent Application EP 18183394.8 dated Sep. 28, 2018.
Extended Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.
European Office Action corresponding to EP 12 152 989.5 dated May 4, 2015.
Australian Office Action corresponding to AU 2009212759 dated May 7, 2015.
Chinese Office Action corresponding to counterpart Int, Appin No. CN 201210212642.9 dated Jun. 3, 2015.
European Office Action corresponding to counterpart Int'l Appln No. EP 04 719 757.9 dated Jun. 12, 2015.
European Office Action corresponding to counterpart Int'l Appln No. EP 13 166 382.5 dated Jun. 19, 2015.
Japanese Office Action corresponding to counterpart Int'l Application No. JP 2010-226908 dated Jun. 26, 2015.
Extended European Search Report corresponding to counterpart Int'l Application No. EP 15 15 5024.1 dated Jul. 17, 2015.
Extended European Search Report corresponding to counterpart Int'l Application No. EP 14 19 2026.4 dated Jul. 17, 2015.
Japanese Office Action corresponding to counterpart Int'l Application No. JP 2011-160126 dated Aug. 10, 2015.

(56) References Cited

OTHER PUBLICATIONS

Extended European Search Report corresponding to counterpart Int'l Application No. EP 14 15 0321.9 dated Sep. 23, 2015.
Extended European Search Report corresponding to counterpart Int'l Application No. EP 11 25 0675.3 dated Oct. 7, 2015.
Extended European Search Report corresponding to counterpart Int'l Application No. EP 11 25 0674.6 dated Oct. 7, 2015.
Extended European Search Report corresponding to counterpart Int'l Application No. EP 12 19 3447.5 dated Oct. 19, 2015.
Canadian Office Action corresponding to counterpart Int'l Application No. CA 2,675,875 dated Oct. 26, 2015.
Japanese Office Action corresponding to counterpart Int'l Application No. JP 2015-005629 dated Oct. 28, 2015.
Japanese Office Action corresponding to counterpart Int'l Application No. JP 2014-245081 dated Oct. 28, 2015.
Canadian Office Action corresponding to counterpart Int'l Application No. CA 2,675,921 dated Oct. 30, 2015.
Chinese Office Action corresponding to counterpart Int'l Application No. CN 201210555570.8 dated Nov. 2, 2015.
Canadian Office Action corresponding to counterpart Int'l Application No. CA 2,676,309 dated Nov. 3, 2015.
Canadian Office Action corresponding to counterpart Int'l Application No. CA 2,676,211 dated Nov. 24, 2015.
Canadian Office Action corresponding to counterpart Int'l Application No. CA 2,676,547 dated Nov. 25, 2015.
Extended European Search Report corresponding to counterpart Int'l Application No. EP 15 17 3809.3 dated. Nov. 25, 2015.
Chinese Office Action corresponding to counterpart Int'l Application No. CN 201210586814.9 dated Dec. 2, 2015.
Extended European Search Report corresponding to counterpart Int'l Application No. EP 12 17 2940.4 dated Dec. 14, 2015.
Chinese First Office Action corresponding to counterpart Int'l Appln. No. CN 201210586826.1 dated Dec. 30, 2015.
Extended European Search Report corresponding to counterpart Int'l Appln. No. EP 15 18 5362.9 dated Feb. 12, 2016.
Extended European Search Report corresponding to counterpart Int'l Appln. No. EP 12 19 7813.4 dated Mar. 7, 2016.
Canadian Office Action corresponding to counterpart Int'l Appln. No. CA 2,676,465 dated Mar. 8, 2016.
Japanese Office Action corresponding to counterpart Int'l Appln. No. JP 2014-245081 dated Mar. 18, 2016.
Japanese Office Action corresponding to counterpart Int'l Appln. No. JP 2015-005629 dated Mar. 18, 2016.
Extended European Search Report corresponding to counterpart Int'l Appln. No. EP 15 19 3549.1 dated Mar. 22, 2016.
International Search Report and Written Opinion corresponding to counterpart Int'l Appln. No. PCT/CN2015/082199 dated Mar. 31, 2016.
Extended European Search Report corresponding to counterpart Int'l Appln. No. EP 15 19 7251.0 dated Apr. 8, 2016.
Extended European Search Report corresponding to counterpart Int'l Appln. No. EP 16 15 0739.7 dated May 17, 2016.
Canadian Office Action corresponding to counterpart Int'l Appln. No. CA 2,716,672 dated May 31, 2016.
Canadian Office Action corresponding to counterpart Int'l Appln. No. CA 2,717,448 dated May 31, 2016.
Canadian Office Action corresponding to counterpart Int'l Appln. No. CA 2,721,951 dated Jun. 1, 2016.
Partial European Search Report corresponding to counterpart Int'l Appln. No. EP 16 15 0287.7 dated Jun. 16, 2016.
Chinese Second Office Action corresponding to counterpart Int'l Appln. No. CN 201210555570.8 dated Jun. 20, 2016.
Chinese First Office Action corresponding to Chinese Appln. No. CN 201410076318.8 dated Jan. 23, 2017.
Extended European Search Report corresponding to European Appln. No. EP 16 18 3184.7 dated Jan. 24, 2017.
Japanese Office Action corresponding to Japanese Appln. No. JP 2016-097807 dated Feb. 14, 2017.
European Office Action corresponding to European Appln. No. EP 12 19 3447.5 dated Apr. 4, 2017.
Chinese First Office Action corresponding to Chinese Appln. No. CN 201410008877.5 dated Apr. 6, 2017.
Extended European Search Report corresponding to European Appln. No. EP 17 15 3714.5 dated May 11, 2017.
Extended European Search Report corresponding to European Appln. No. EP 17 15 8519.3 dated May 19, 2017.
Extended European Search Report corresponding to European Appln. No. EP 17 15 7606.9 dated May 22, 2017.
European Office Action corresponding to European Appln. No. EP 11 25 0674.6 dated May 23, 2017.
Canadian Office Action corresponding to Canadian Appln. No. CA 2,743,402 dated May 30, 2017.
Extended European Search Report corresponding to European Application No. EP 07 25 3905.9, completed Jan. 29, 2008; dated Feb. 7, 2008; (7 Pages).
International Search Report corresponding to International Application No. PCT-US08-58185, completed Sep. 4, 2008; dated Sep. 9, 2008; (2 Pages).
International Search Report corresponding to International Application No. PCT-US08-59859, completed Sep. 14, 2008; dated Sep. 18, 2008; (2 Pages).
Extended European Search Report corresponding to European Application No. EP 07 25 3807.7, completed Nov. 7, 2008; dated Nov. 26, 2008; (11 Pages).
Extended European Search Report corresponding to European Application No. EP 09 25 2049.3, completed Dec. 11, 2009; dated Jan. 12, 2010; (3 Pages).
Extended European Search Report corresponding to European Application No. EP 09 25 2050.1, completed Dec. 23, 2009; dated Jan. 21, 2010; (3 Pages).
Extended European Search Report corresponding to European Application No. EP 09 25 2051.9, completed Dec. 21, 2009; dated Jan. 28, 2010; (3 Pages).
Extended European Search Report corresponding to European Application No. EP 09 25 2052.7, completed Nov. 16, 2009; dated Nov. 24, 2009; (3 Pages).
Extended European Search Report corresponding to European Application No. EP 09 25 2053.5, completed Nov. 24, 2009; dated Dec. 1, 2009; (3 Pages).
Extended European Search Report corresponding to European Application No. EP 09 25 2054.3, completed Jan. 7, 2010; dated Jan. 22, 2010; (3 Pages).
Extended European Search Report corresponding to European Application No. EP 09 25 2056.8 , completed Jan. 8, 2010; dated Feb. 5, 2010; (3 Pages).
Extended European Search Report corresponding to European Application No. EP 10 25 0497.4, completed May 4, 2010; dated May 12, 2010; (6 Pages).
Extended European Search Report corresponding to European Application No. EP 10 25 2079.8, completed Mar. 8, 2011; dated Mar. 17, 2011; (3 Pages).
European Search Report corresponding to European Application No. EP 05 81 0218.7, completed Apr. 18, 2011; dated May 20, 2011; (3 pages).
European Search Report corresponding to European Application No. EP 05 80 7612.6, completed May 2, 2011; dated May 20, 2011; (3 pages).
Extended European Search Report corresponding to European Application No. EP 10 25 1737.2, completed May 9, 2011; dated May 20, 2011; (4 pages).
Extended European Search Report corresponding to European Application No.EP 11 25 0214.1, completed May 25, 2011; dated Jun. 1, 2011; (3 Pages).
Extended European Search Report corresponding to European Application No. EP 11 00 2681.2, completed May 31, 2011; dated Jun. 10, 2011; (3 Pages).
European Search Report corresponding to European Application No. EP 05 80 2686.5, completed Jan. 9, 2012; dated Jan. 18, 2012; (3 Pages).
Extended European Search Report corresponding to European Application No. EP 12 15 1313.9, completed Mar. 20, 2012 and dated Apr. 12, 2012; (5 Pages).

(56) References Cited

OTHER PUBLICATIONS

Extended European Search Report corresponding to European Application No. EP 12 16 1291.5, completed Apr. 24, 2012 and dated May 4, 2012; (5 Pages).
Extended European Search Report corresponding to European Application No. EP 12 16 5891.8, completed Jun. 12, 2012 and dated Jun. 20, 2012; (6 Pages).
Extended European Search Report corresponding to European Application No. EP 12 16 2288.0, completed Jun. 4, 2012 and dated Jul. 7, 2012; (6 Pages).
Extended European Search Report corresponding to European Application No. EP 12 16 4955.2, completed Aug. 23, 2012 and dated Sep. 4, 2012; (5 Pages).
Extended European Search Report corresponding to European Application No. EP 11 25 0754.6, completed Oct. 22, 2012 and dated Oct. 31, 2012; (6 Pages).
Extended European Search Report corresponding to European Application No. EP 12 18 6401.1, completed Nov. 22, 2012 and dated Nov. 30, 2012; (7 Pages).
Extended European Search Report corresponding to European Application No. EP 12 18 6448.2, completed Nov. 28, 2012 and dated Dec. 10, 2012; (6 Pages).
Extended European Search Report corresponding to European Application No. EP 12 19 1706.6, completed Dec. 19, 2012 and dated Jan. 8, 2013; (6 Pages).
Extended European Search Report corresponding to EP 12 19 8745.7, completed Mar. 19, 2013 and dated Apr. 11, 2013; (8 Pages).
Extended European Search Report corresponding to EP 12 15 2989.5, completed Apr. 9, 2013 and dated Apr. 18, 2013; (9 Pages).
Extended European Search Report corresponding to EP 08 73 2820.9, completed Jul. 2, 2013 and dated Jul. 9, 2013; (10 Pages).
Extended European Search Report corresponding to EP 13 17 2008.8, completed Aug. 14, 2013 and dated Aug. 28, 2013; (8 Pages).
Extended European Search Report corresponding to EP 13 16 6382.5, completed Nov. 19, 2013 and dated Nov. 28, 2013; (8 Pages).
Extended European Search Report corresponding to EP 11 25 0194.5, completed Nov. 25, 2013 and dated Dec. 3, 2013; (8 Pages).
Extended European Search Report corresponding to EP 10 25 1798.4, completed Dec. 12, 2013 and dated Jan. 2, 2014; (9 Pages).
"Salute II Disposable Fixation Device", Technique Guide—Laparoscopic and Open Inguinal and Ventral Hernia Repair; Davol, A Bard Company, 2006; (7 Pages).
Extended European Search Report corresponding to EP 10 25 2112.7, completed Jul. 29, 2014 and dated Aug. 5, 2014; (8 Pages).
Extended European Search Report corresponding to EP 14 15 1673.2, completed Apr. 25, 2014 and dated May 8, 2014; (8 Pages).
Japanese Office Action corresponding to JP 2011-160130 dated Dec. 1, 2014.
Chinese Office Action corresponding to CN 201210015011.8 dated Jan. 4, 2015.
Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.

* cited by examiner

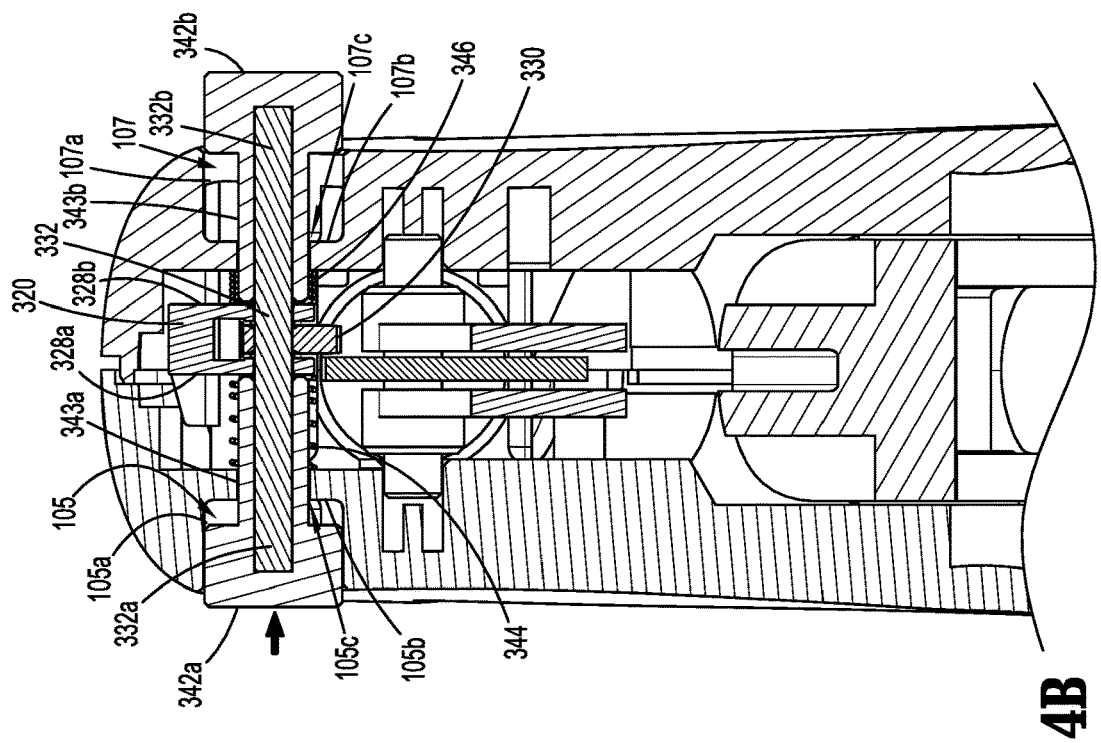
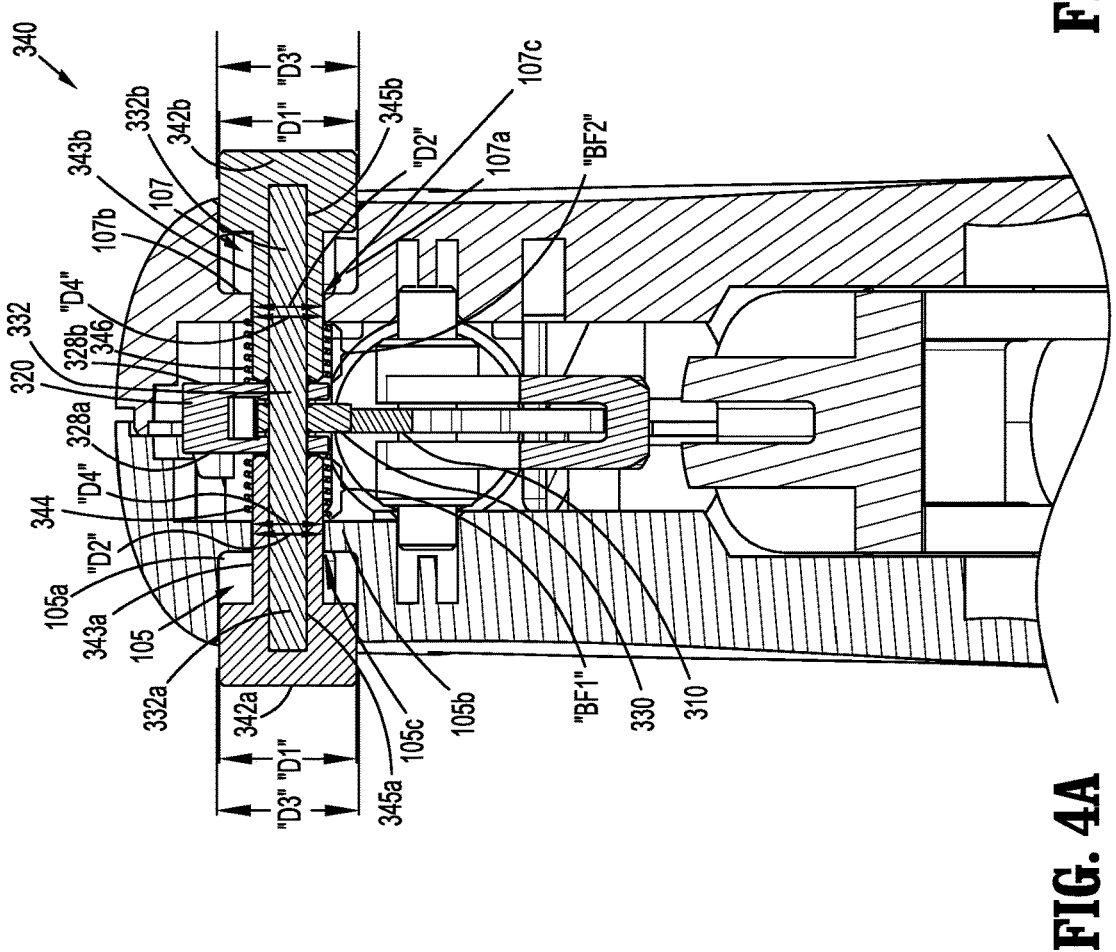
FIG. 4A
FIG. 4B

ENDOSCOPIC SURGICAL CLIP APPLIER

CROSS-REFERENCE TO RELATED APPLICATIONS

This application claims the benefit of and priority to U.S. Provisional Patent Application No. 62/462,407 filed Feb. 23, 2017, the entire disclosure of which is incorporated by reference herein.

BACKGROUND

Technical Field

The present disclosure relates generally to surgical clip appliers. More particularly, the present disclosure relates to endoscopic surgical clip appliers having a release switch for a ratchet assembly thereof.

Description of Related Art

Endoscopic surgical staplers and surgical clip appliers are used for a number of minimally invasive or endoscopic surgical procedures. Typically in a minimally invasive surgical procedure, a tube or cannula device is extended into the patient's body through an entrance incision to provide an access port. The port allows the surgeon to insert a number of different surgical instruments therethrough for performing surgical procedures far removed from the incision.

Endoscopic surgical clip appliers are capable of applying a single or multiple surgical clips during a minimally invasive surgical procedure. Applying surgical clips usually involves compressing the clip over a vessel. Once applied to the vessel, the compressed surgical clip terminates the flow of fluid therethrough. Terminating the flow of fluid through a vessel typically requires complete formation of the surgical clip.

During certain endoscopic procedures, it may be desirable and/or necessary to partially form clips. For example, a partially formed clip may be used to secure a catheter around tissue during a cholangiogram or other medical procedure.

Accordingly, a need exists for endoscopic surgical clip appliers that provide a clinician with a convenient way to partially form surgical clips.

SUMMARY

The present disclosure relates to endoscopic surgical clip appliers that allow a clinician to choose whether to partially or completely form surgical clips.

According to an aspect of the present disclosure, an endoscopic surgical clip applier includes an endoscopic assembly and a handle assembly. The endoscopic assembly includes a shaft assembly and a pair of jaw members operatively coupled to, and extending from the shaft assembly. The handle assembly includes a housing selectively connectable to the endoscopic assembly. A fixed handle extends from the housing, and a trigger is pivotally connected to the fixed handle. A drive bar is disposed within the housing of the handle assembly and is operatively coupled to the trigger and to the pair of jaw members to move the pair of jaw members between a spaced apart configuration and an approximated configuration upon actuation of the trigger. A ratchet assembly is also disposed within the housing of the handle assembly. The ratchet assembly includes a first rack operatively coupled to the drive bar. The first rack defines a plurality of first rack teeth. A second rack is operatively coupled to the drive bar, spaced apart from the first rack. The second rack defines a plurality of second rack teeth. A pawl housing is slidably mounted within the housing of the handle assembly. The pawl housing has a first pawl selectively engageable with the plurality of first rack teeth of the first rack. The pawl housing is transversely slidable between a first position and a second position. A second pawl is movably mounted within the housing of the handle assembly. The second pawl is selectively engageable with the plurality of second rack teeth of the second rack. In the first position of the pawl housing, the first pawl is in registration with the plurality of first rack teeth of the first rack to prohibit reversal of a direction of movement of the trigger until the first pawl is disposed beyond a proximal end or a distal end of the first rack. In the second position of the pawl housing, the first pawl is out of registration with the plurality of first rack teeth of the first rack to permit reversal of the direction of movement of the trigger after the second pawl is disposed distally beyond a distal end of the second rack or proximally beyond a proximal end of the second rack.

In embodiments, the first rack includes a first length between the distal end and the proximal end thereof and the second rack includes a second length between the distal end and the proximal end thereof. The second length of the second rack may be less than the first length of the first rack.

The ratchet assembly may include a release switch at least partially supported within the housing of the handle assembly and operatively associated with the pawl housing. The release switch may be selectively actuatable to move the pawl housing from the first position thereof to the second position thereof, wherein in the second position of the pawl housing, the pawl housing is moved transversely relative to the first rack to disengage the first pawl from the plurality of first rack teeth of the first rack.

In embodiments, the second pawl is selectively engageable with the plurality of second rack teeth of the second rack in a first position thereof.

In some embodiments, the ratchet assembly further includes a distal well disposed adjacent the distal end of the first rack, and the pawl housing is located in the distal well in an un-actuated position of the trigger.

The ratchet assembly may further include a proximal well disposed between the proximal end of the first rack and the distal end of the second rack, and the second pawl is located in the proximal well in the un-actuated position of the trigger.

In embodiments, the first rack is disposed in a position distal of the second rack.

When the release switch is actuated, the second pawl may maintain registration with the plurality of second rack teeth of the second rack, in the first position thereof, until the second pawl is disposed in the proximal well or until the second pawl is disposed proximally beyond the proximal end of the second rack.

In some embodiments, the drive bar is longitudinally movable upon actuation of the trigger. As the drive bar is moved longitudinally in a first direction, and the release switch is not actuated, the first pawl and the second pawl are moved over the plurality of first rack teeth and the plurality of second rack teeth of the first and the second racks, respectively, such that longitudinal movement of the drive bar in a second, opposite, direction is prevented until the first pawl is disposed in the distal well and the second pawl is disposed in the proximal well or until the first pawl is disposed at the proximal end of the first rack and the second pawl is disposed proximally beyond the proximal end of the second rack. As the drive bar is moved longitudinally in a first direction, and the release switch is actuated to move the pawl housing to the second position, longitudinal movement of the drive bar in a second, opposite, direction is prevented until the second pawl is disposed in the proximal well or until the second pawl is disposed proximally beyond the proximal end of the second rack.

In embodiments, as the drive bar is moved longitudinally in the first direction, and the release switch is actuated to move the pawl housing to the second position, the second pawl is disposed beyond the proximal end of the second rack as the trigger reaches a partially actuated position, wherein the drive bar is longitudinally movable in the second, opposite, direction, as the trigger reaches a fully un-actuated position from the partially actuated position The endoscopic assembly may further include a plurality of surgical clips slidably disposed within the shaft assembly and selectively formable between the pair of jaw members. When the pawl housing is in the first position, the first pawl is in registration with the first rack disposed on the drive bar such that upon actuation of the trigger, the trigger is prevented from reversing the direction of movement thereof until the trigger is moved to a fully actuated position and a distal most surgical clip of the plurality of surgical clips is fully formed between the pair of jaw members.

In some embodiments, when the pawl housing is in the second position, the first pawl is out of registration with the first rack disposed on the drive bar such that when the second pawl is disposed beyond the proximal end of the second rack and the trigger is moved to the partially actuated position, the trigger is capable of reversing the direction of movement thereof such that the distal most surgical clip of the plurality of surgical clips is partially formed between the pair of jaw members.

The pawl housing may define a channel therein, and the first pawl may be located within the channel of the pawl housing.

In embodiments, the ratchet assembly includes a switch pin. The pawl housing defines a central slot therein configured to locate the switch pin, and the switch pin slidably extends through the channel of the pawl housing and the first pawl to support the first pawl within the channel of the pawl housing.

The release switch may include a first end cap and a second end cap, and a first side of the housing includes a first switch slot configured to slidably receive the first end cap of the release switch and a second side of the housing includes a second switch slot configured to slidably receive the second end cap of the release switch.

In some embodiments, the first end cap of the release switch is supported on a first end of the switch pin, on a first side of the pawl housing, and the second end cap of the release switch is supported on a second end of the switch pin, on a second, opposite side of the pawl housing, such that the release switch is accessible via the first and second end caps from the first and second sides of the pawl housing, respectively, to actuate the release switch.

In embodiments, the ratchet assembly further includes a first pawl spring and a second pawl spring supported within the housing of the handle assembly. The first pawl spring is configured to bias the first pawl into engagement with the plurality of first rack teeth of the first rack and the second pawl spring being configured to bias the second pawl into engagement with the plurality of second rack teeth of the second rack.

According to another aspect of the present disclosure, an endoscopic surgical clip applier includes an endoscopic assembly and a handle assembly. The endoscopic assembly includes a shaft assembly and a pair of jaw members operatively coupled to, and extending from the shaft assembly. The handle assembly includes a housing selectively connectable to the endoscopic assembly, a fixed handle extending from the housing, and a trigger pivotally connected to the fixed handle. A drive bar is disposed within the housing of the handle assembly and is operatively coupled to the trigger and the pair of jaw members. The drive bar is longitudinally movable to move the pair of jaw members between a spaced apart configuration and an approximated configuration upon actuation of the trigger. A ratchet assembly is also disposed within the housing of the handle assembly. The ratchet assembly includes a first rack defined on a top portion of the drive bar. The first rack includes a first length between a distal end and a proximal end thereof. A second rack is defined on the top portion of the drive bar. The second rack includes a second length between a distal end and a proximal end thereof. The second length of the second rack is less than the first length of the first rack. A first pawl is movable mounted within the handle assembly and is selectively engageable with the first rack. The first pawl is transversely slidable between a first position and a second position. A release switch is at least partially supported within the housing of the handle assembly and is operatively associated with the first pawl. The release switch is selectively actuatable to transversely move the first pawl from the first position thereof to the second position thereof. In the first position of the first pawl, the first pawl is in registration with the first rack to prohibit reversal of a direction of movement of the trigger until the drive bar is moved a first distance equal to the first length of the first rack. In the second position of the first pawl, the first pawl is moved transversely relative to the first rack to disengage the first pawl from the first rack such that reversal of the direction of movement of the trigger is prohibited until the drive bar is moved a second distance equal to the second length of the second rack.

In embodiments, the ratchet assembly includes a second pawl movable mounted within the handle assembly and selectively engageable with the second rack. Upon movement of the trigger, reversal of the direction of movement of the trigger is prohibited until the second pawl is disposed distally beyond the distal end of the second rack or proximally beyond the proximal end of the second rack.

BRIEF DESCRIPTION OF THE DRAWINGS

Particular embodiments of endoscopic surgical clip appliers are described herein with reference to the drawings wherein:

FIG. 4A is a cross-sectional, plan view, as taken through 4A-4A of FIG. 1, illustrating the ratchet assembly in a first position;

FIG. 4B is a cross-sectional, plan view, as taken through 4A-4A of FIG. 1, illustrating the ratchet assembly in a second position;

DETAILED DESCRIPTION OF EMBODIMENTS

Figure 1:
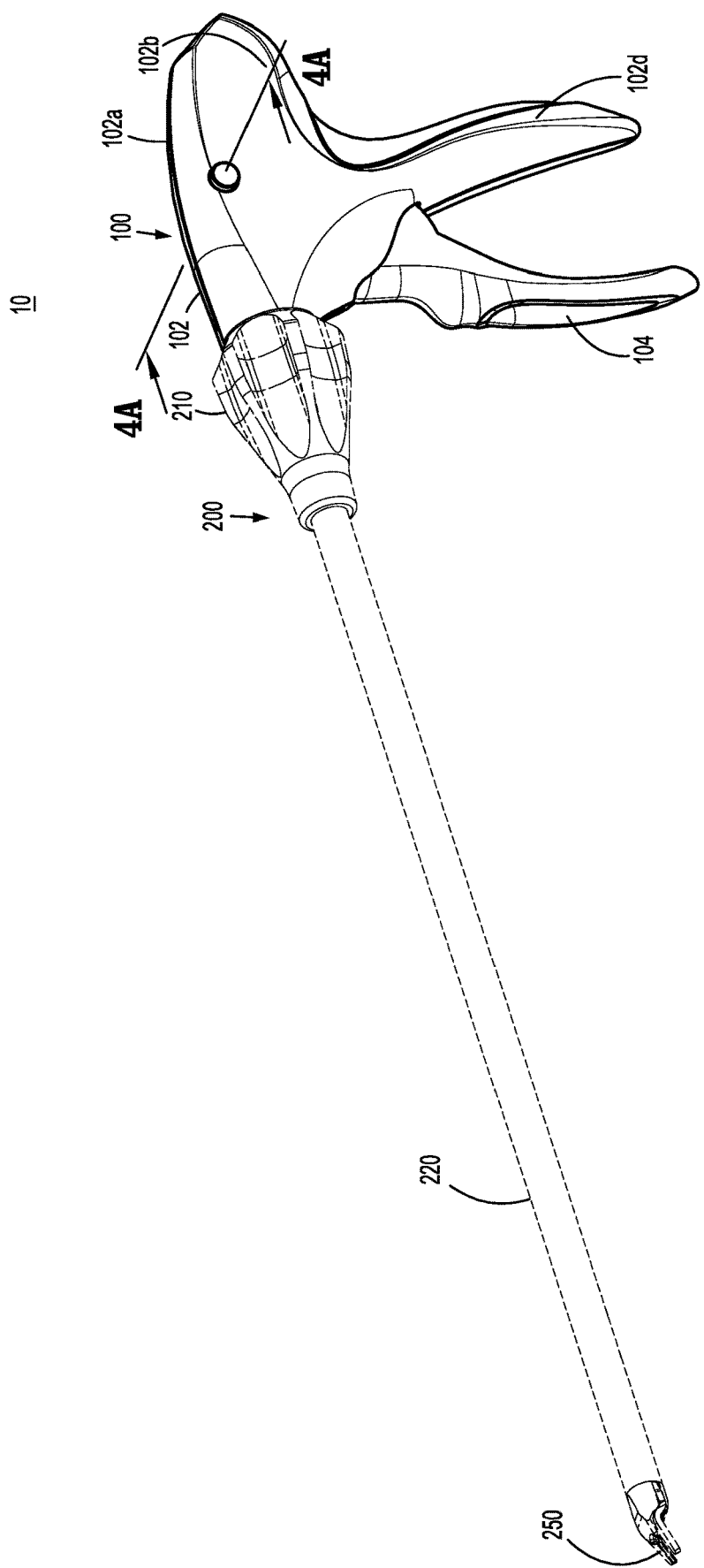
FIG. 1 is a perspective view of an endoscopic surgical clip applier, according to the present disclosure including an endoscopic assembly and a handle assembly.

In accordance with the present disclosure, an endoscopic surgical clip applier includes a ratchet assembly having a first rack, with a first length, operatively associated with a pawl housing having a first pawl. A second rack, with a second length less than the first length of the first rack, is operatively associated with a second pawl. A release switch is operatively associated with the pawl housing and the first pawl. In embodiments, upon actuation of a trigger, the first and second pawls are configured to engage a plurality of first and second rack teeth of the first and second racks, respectively, to prohibit release and reversal of a direction of movement of the trigger until the first and second pawls are disposed within respective clearances of the first and second racks. In embodiments, the release switch is selectively actuatable to move the first pawl out of registration or engagement with the plurality of first rack teeth of the first rack such that the direction of movement of the trigger may be reversed early once the second pawl has traversed the second, lesser, length of the second rack. It is contemplated that the release switch may be useful to partially form clips, if desired for example, to secure a catheter around tissue during a cholangiogram or other medical procedure.

Embodiments of endoscopic surgical clip appliers, in accordance with the present disclosure, will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Referring now to FIGS. 1-6, an endoscopic surgical clip applier in accordance with an embodiment of the present disclosure is generally designated as 10. Surgical clip applier 10 generally includes a handle assembly 100 and an endoscopic assembly 200 that extends distally from handle assembly 100. Generally, endoscopic assembly 200 includes a hub assembly 210, a shaft assembly 220 extending from hub assembly 210, and a pair of jaws 250 pivotally connected to a distal end of shaft assembly 220. Optionally, at least one disposable surgical clip cartridge assembly (not shown) may be selectively loadable into shaft assembly 220 of endoscopic assembly 200.

Figure 2A:
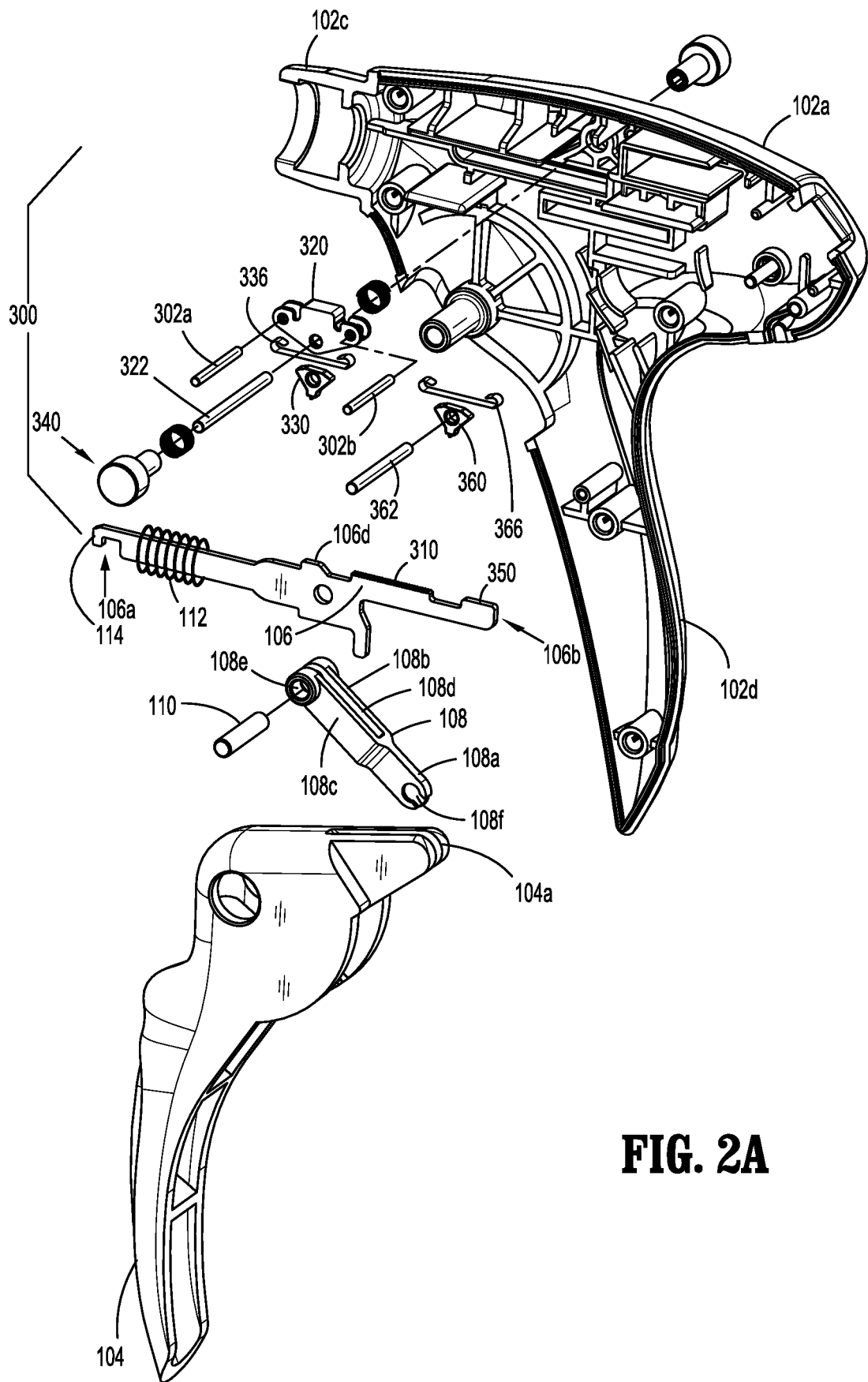
FIG. 2A is a perspective view, with parts separated, of the handle assembly of FIG. 1.
Figure 2B:
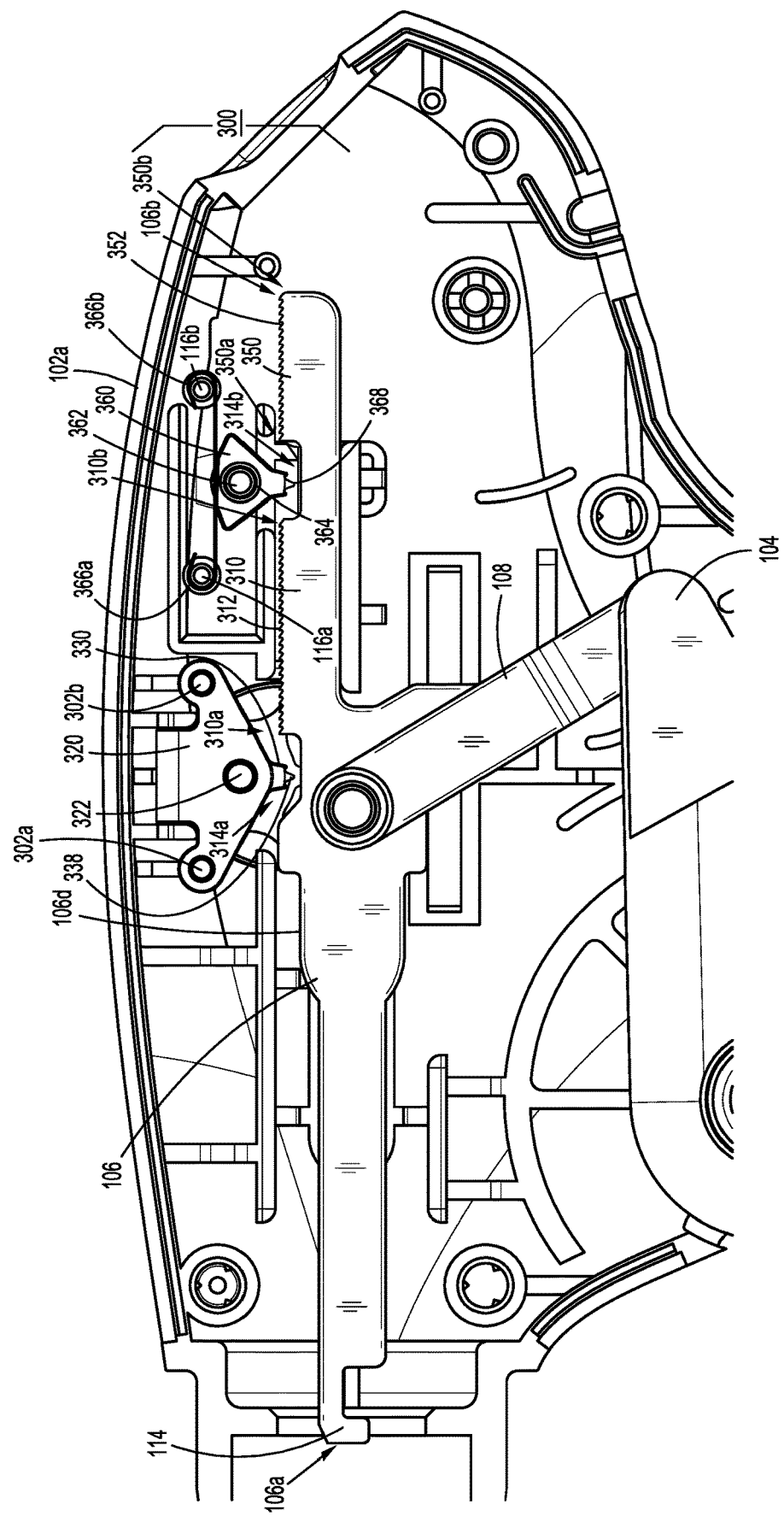
FIG. 2B is a side view, of the handle assembly of FIG. 1 with at least a housing half-section removed therefrom, illustrating a ratchet mechanism thereof.

Referring now to FIGS. 1-2B, handle assembly 100 of surgical clip applier 10 includes a housing 102 having a first or right side half-section 102a and a second or left side half-section 102b. Housing 102 of handle assembly 100 further includes or defines a nose 102c for supporting hub assembly 210 of endoscopic assembly 200, and a fixed handle 102d.

Housing 102 of handle assembly 100 may be formed of a suitable polymer, plastic or thermoplastic material. It is further contemplated that housing 102 of handle assembly 100 may be fabricated from stainless steel or the like.

Handle assembly 100 includes a trigger 104 pivotably supported between right side half-section 102a and left side half-section 102b of housing 102. Trigger 104 is pivotably movable in a first direction such that the trigger 104 and the fixed handle 102d are approximated and pivotably movable in a second, opposite, direction such that the trigger 104 and the fixed handle 102d are spaced-apart.

A drive bar 106 is supported within the housing 102 of the handle assembly 100. The drive bar 106 may be a substantially flat member having a distal end portion 106a and a proximal end portion 106b. The distal end portion 106a of drive bar 106 includes a hook member 114 that is provided to mate with a feature of endoscopic assembly 200. The drive bar 106 is operatively coupled to the trigger 104 and the pair of jaws 250 of endoscopic assembly 200 to move the pair of jaws 250 between a spaced-apart configuration and an approximated configuration upon actuation of the trigger 104. Specifically, the handle assembly 100 includes a wishbone link 108 configured to couple the trigger 104 and the drive bar 106. Wishbone link 108 includes a first end portion having a tail 108a and a second end portion having a first arm and a second arm 108b, 108c spaced-apart to define a space 108d therebetween. The tail 108a of the wishbone link 108 is pivotably connected to trigger 104 through a trigger slot 104a. Specifically, tail 108a of wishbone link 108 includes an opening 108f configured for pivotably locating a pin (not specifically shown) defined within trigger slot 104a. The space 108d between the first and second arms 108b, 108c is configured to receive the drive bar 106. The first and second arms 108b, 108c of wishbone link 108, and the drive bar 106 includes corresponding apertures 108e, 106c, respectively, configured to locate a drive bar pin 110 to pivotably connect the wishbone link 108 and the drive bar 106. The wishbone link 108 is configured to translate the pivotal movement of the trigger 104 into longitudinal movement of the drive bar 106, as will be detailed below.

The drive bar 106 is configured to move one or more driving structures to load, and actuate the pair of jaws 250 to form a clip (not shown) fully or partially, and then reset to an initial position for the next clip application. To achieve this, a biasing member, such as, for example, a first return spring 112 is disposed to surround the drive bar 106 adjacent the distal end portion 106a such that, after the trigger 104 is actuated and the wishbone link 108 advances the drive bar 106 in a longitudinal or distal manner, the first return spring 112 is provided to return the drive bar 106 and the trigger 104 to its original position for the next clip application.

With continued reference to FIGS. 2A and 2B, surgical clip applier 10 includes a ratchet assembly 300 disposed within housing 102 of handle assembly 100. The ratchet assembly 300 generally includes a first rack 310, a pawl housing 320 having a first pawl 330 operatively associated with first rack 310, a release switch 340 at least partially supported within housing 102 of handle assembly 100 and operatively associated with pawl housing 320, and in turn first pawl 330, a second rack 350, and a second pawl 360 operatively associated with second rack 350.

As shown in FIG. 2B, the first and second racks 310, 350 are supported by or are provided on a top surface 106d of the drive bar 106. The first rack 310 includes a distal end 310a and a proximal end 310b. The first rack 310 defines a plurality of first rack teeth 312 in series between the distal end 310a and the proximal end 310b thereof. Similarly, the second rack 350 includes a distal end 350a and a proximal end 350b. The second rack 350 defines a plurality of second rack teeth 352 in series between the distal end 350a and the proximal end 350b thereof.

The top surface 106d of the drive bar 106 also includes a distal clearance or well 314a located adjacent the distal end 310a of the first rack 310 and a proximal clearance or well 314b located between the proximal end 310b of the first rack 310 and the distal end 350a of the second rack 350. The distal well 314a is configured to receive the first pawl 330 and the proximal well 314b is configured to receive the second pawl 360, when ratchet assembly 300 is in an initial and/or reset position, as shown in FIG. 2B and as will be detailed further below.

Figure 3A:
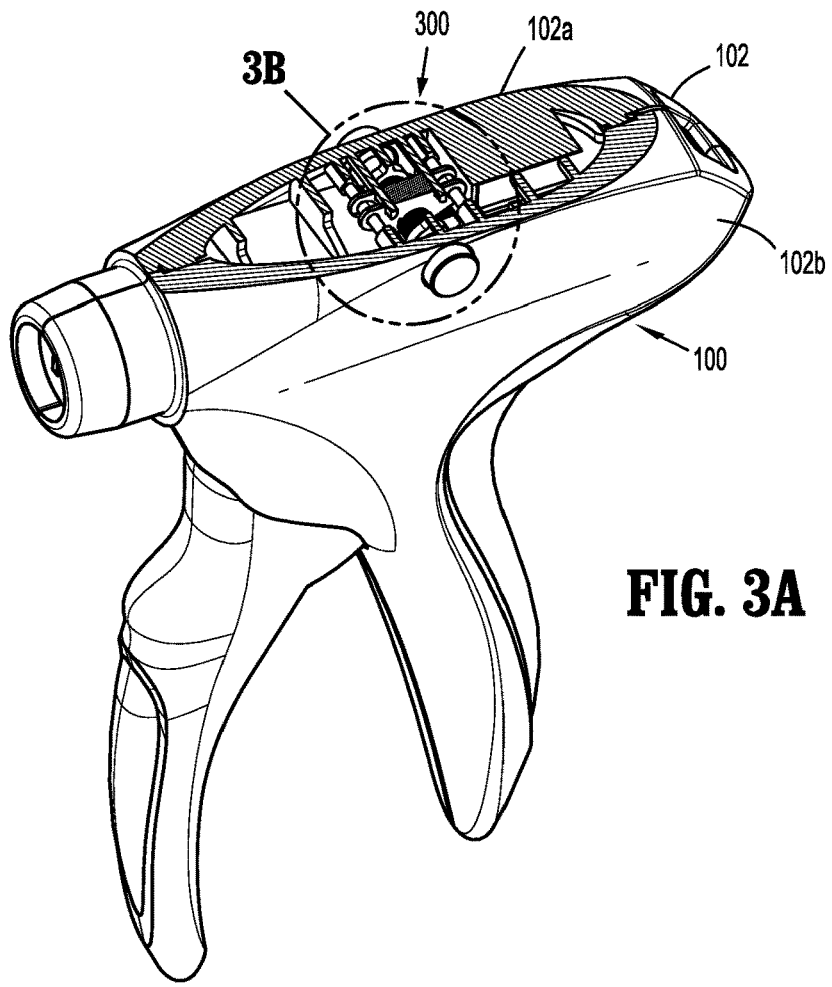
FIG. 3A is a perspective view, of the handle assembly of FIG. 1 with at least a top housing portion removed or cut away therefrom, illustrating the ratchet assembly thereof.
Figure 3B:
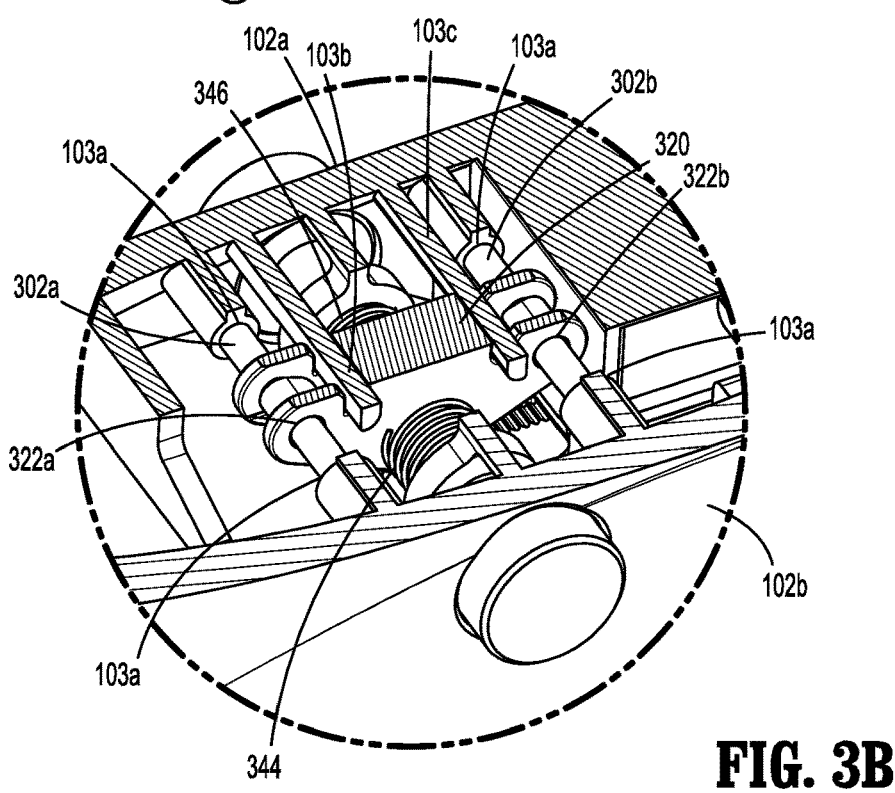
FIG. 3B is an enlarged perspective view of the indicated area of detail of FIG. 3A.
Figure 3C:
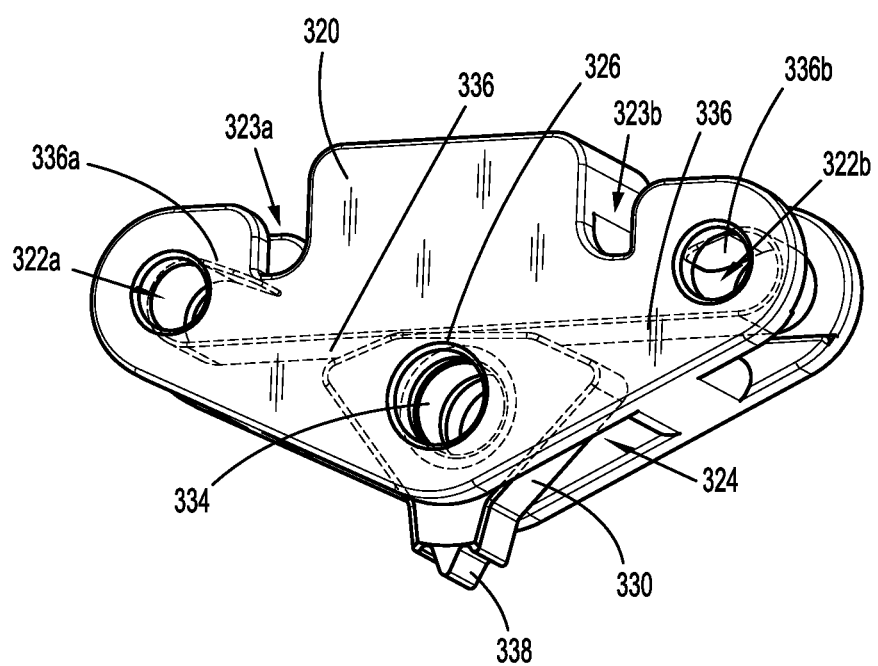
FIG. 3C is an enlarged perspective view illustrating a pawl housing including a pawl of the ratchet assembly of the handle assembly of FIG. 1.

With continued reference to FIGS. 2A and 2B, and additional reference to FIGS. 3A-3C, pawl housing 320 is slidably mounted within the handle assembly 100 between the right side half-section 102a and the left side half-section 102b of the housing 102. Specifically, the ratchet assembly 300 includes a distal support pin 302a and a proximal support pin 302b and the pawl housing 320 includes a distal support slot 322a and a proximal support slot 322b configured to locate the distal support pin 302a and the proximal support pin 302b, respectively. The distal support pin 302a and the proximal support pin 302b are mounted onto a plurality of corresponding slots 103a within the housing 102 to slidably mount the pawl housing 320 within the housing 102 of the handle assembly 100. In embodiments, as best illustrated in FIG. 3C, pawl housing 320 further includes a first guide channel 323a and a second guide channel 323b configured for locating a first guide feature 103b and a second guide feature 103c, respectively, extending from at least one of the right side half-section 102a or the left side half-section 102b of housing 102. It is contemplated that the first and second guide features 103b, 103c are provided to align the distal and proximal support slots 322a, 322b of the pawl housing 320 with the plurality of corresponding slots 103a of housing 102 for locating the distal and proximal support pins 302a, 302b, respectively.

As shown in FIG. 3C, the pawl housing 320 further defines a channel or recess 324 configured to locate the first pawl 330 therein. First pawl 330 is pivotably connected to the pawl housing 320 by a switch pin 332 (see FIG. 2A) at a location wherein first pawl 330 is in substantial operative engagement/registration with the first rack 310. The switch pin 332 extends through a central slot 326 defined in the pawl housing 320 and a corresponding slot 334 defined in the first pawl 330. The ratchet assembly 300 further includes a first pawl spring 336 disposed within the pawl housing 320 and configured to vertically bias first pawl 330 into operative engagement or registration with the first rack 310 (see FIG. 5A). Specifically, the first pawl spring 336 includes a distal hook 336a configured to latch onto the distal support pin 302a (see FIG. 2A) and a proximal hook 336b configured to latch onto the proximal support pin 302b (see FIG. 2A). It is contemplated that first pawl spring 336 is positioned in a manner configured to maintain a first pawl tooth 338 of the first pawl 330 in registration or engagement with the plurality of first rack teeth 312 (see FIG. 5A), as well as to maintain the first pawl 330 in a rotated or canted position.

Returning briefly back to FIGS. 2A and 2B, second pawl 360 is pivotably mounted within the handle assembly 100 between the right side half-section 102a and the left side half-section 102b of the housing 102 by a second pawl pin 362 at a location wherein the second pawl 360 is in substantial operative engagement/registration with the second rack 350. The second pawl pin 362 extends through a slot 364 defined in the second pawl 360. The ratchet assembly 300 further includes a second pawl spring 366 configured to vertically bias the second pawl 360 into operative engagement/registration with the second rack 350. The second pawl spring 366 includes a distal hook 366a and a proximal hook 366b configured to latch onto a pair of support pins 116a, 116b of housing 102, respectively. It is contemplated that second pawl spring 366 is positioned in a manner configured to maintain a second pawl tooth 368 of the second pawl 360 in registration or engagement with the plurality of second rack teeth 352 (see FIG. 5A), as well as to maintain the second pawl 360 in a rotated or canted position.

With reference to FIGS. 4A and 4B, ratchet assembly 300 further includes release switch 340 at least partially supported within housing 102 of handle assembly 100. As noted above, release switch 340 is operatively associated with pawl housing 320 and is operable to selectively move pawl housing 320, and in turn first pawl 330, into or out of registration with the plurality of first rack teeth 312 of first rack 310.

Specifically, release switch 340 includes a first end cap 342a slidably supported on a first end portion 332a of switch pin 332 and a second end cap 342b slidably supported on a second end portion 332b of switch pin 332. First end cap 342a has a first extension 343a and defines a substantially "T" shaped profile. First end cap 342a defines a first channel or bore 345a therein, sized and configured to slidably receive the first end portion 332a of switch pin 332. Similarly, second end cap 342b has a second extension 343b and defines a substantially "T" shaped profile. Second end cap 342b defines a second channel or bore 345b therein, sized and configured to slidably receive the second end portion 332b of switch pin 332.

In embodiments, first and second end caps 342a, 342b are cylindrically shaped, each including a first diameter "D1". Similarly, in embodiments, first and second extensions 343a, 343b are cylindrically shaped, each including a second diameter "D2" that is less than the first diameter "D1". Alternatively, first and second end caps 342a, 342b and first and second extensions 343a, 343b, respectively, may include various shapes and sizes as necessary for its intended purpose.

Right side half-section 102a of housing 102 includes a first switch slot or bore 105 sized and configured to slidably receive the first end cap 342a and left side half-section 102b of housing 102 includes a second switch slot or bore 107 sized and configured to slidably receive the second end cap 342b. Once first and second end caps 342a, 342b are received within first and second switch slots 105, 107, respectively, first and second extensions 343a, 343b are provided to be in contact with a first side 328a and a second side 328b of pawl housing 320, respectively.

In embodiments, first and second switch slots 105, 107 each include a first portion 105a, 107a, respectively, defining a third diameter "D3" that is slightly larger than the first diameters "D1" of first and second end caps 342a, 342b to enable slidable insertion of first and second end caps 342a, 342b into first portions 105a, 107a of respective first and second switch slots 105, 107 without significant play or clearance therebetween. First and second switch slots 105, 107 each further include an internal wall 105b, 107b. Internal walls 105b, 107b of slots 105, 107, respectively, are provided to prevent slidable insertion of first and second end caps 342a, 342b beyond first portions 105a, 107a, respectively. Internal walls 105b, 107b of slots 105, 107, respectively, each define an opening 105c, 107c, respectively, defining a fourth diameter "D4" that is less than the third diameter "D3" of first portions 105a, 107a. The fourth diameter "D4" of each opening 105c, 107c is slightly larger than the second diameters "D2" of the first and second extensions 343a, 343b to enable slidable insertion of the first and second extensions 343a, 343b into the openings 105c, 107c without significant play or clearance therebetween.

First and second end caps 342a, 342b project from first and second switch slots 105, 107, respectively, and may be actuated by a finger of a user to actuate release switch 340. It is contemplated that first portions 105a, 107a, of first and second switch slots 105, 107, respectively, provide sufficient runway to enable first and second end caps 342a, 342b, respectively, to move therethrough to actuate release switch 340.

In embodiments, housing 102 of handle assembly 100 may be provided with guard walls (not specifically shown) surrounding the first and second end caps 342a, 342b in order to inhibit inadvertent actuation of release switch 340. In some embodiments, the first and second end caps 342a, 342b may be flush with an outer surface of housing 102 of handle assembly 100 in order to also inhibit inadvertent actuation of release switch 340.

Release switch 340 is movable, upon actuation of first or second end caps 342a, 342b, between the first position (see FIG. 4A) in which first pawl 330 is in or moved into operative engagement/registration with the plurality of first rack teeth 312 of first rack 310, and the second position (see FIG. 4B) in which first pawl 330 is out of or moved out of operative engagement/registration with the plurality of first rack teeth 312 of first rack 310.

It is contemplated that release switch 340, and in turn ratchet assembly 300, defaults to the first position, in which first pawl 330 is engaged with/in registration with the plurality of first rack teeth 312. To that end, release switch 340 includes a first biasing member 344 supported on first extension 343a of first end cap 343a, extending between a first side 328a of pawl housing 320 and internal wall 105b of first switch slot 105, and includes a second biasing member 346 supported on second extension 343b of second end cap 342b, extending between a second side 328b of pawl housing 320 and internal wall 107b of second switch slot 107. The first biasing member 344 includes a first biasing force "BF1" and is provided to bias or urge second end cap 342b away from internal wall 107b of second switch slot 107. Similarly, the second biasing member 346 includes a second biasing force "BF2" and is provided to bias or urge first end cap 342a away from internal wall 105b of first switch slot 105. Together, first and second biasing members 344, 346 cooperate to maintain pawl housing 320 in the first position such that pawl housing 320 is centered relative to first rack 310 (see FIG. 4A) and the first pawl 330 is engagable with the first rack 310 to restrict longitudinal movement of drive bar 106.

As noted above, release switch 340 is actuatable from the first position towards the second position, upon actuation of the first or second end caps 342a, 342b. Accordingly, for illustrative purposes, the use of release switch 340, and generally ratchet assembly 300, will be detailed with reference to actuation of the first end cap 342a.

With brief reference to FIG. 2B, in the initial and/or reset position, the first pawl 330 is disposed within distal well 314a and the second pawl 360 is disposed within proximal well 314b.

Figure 5A:
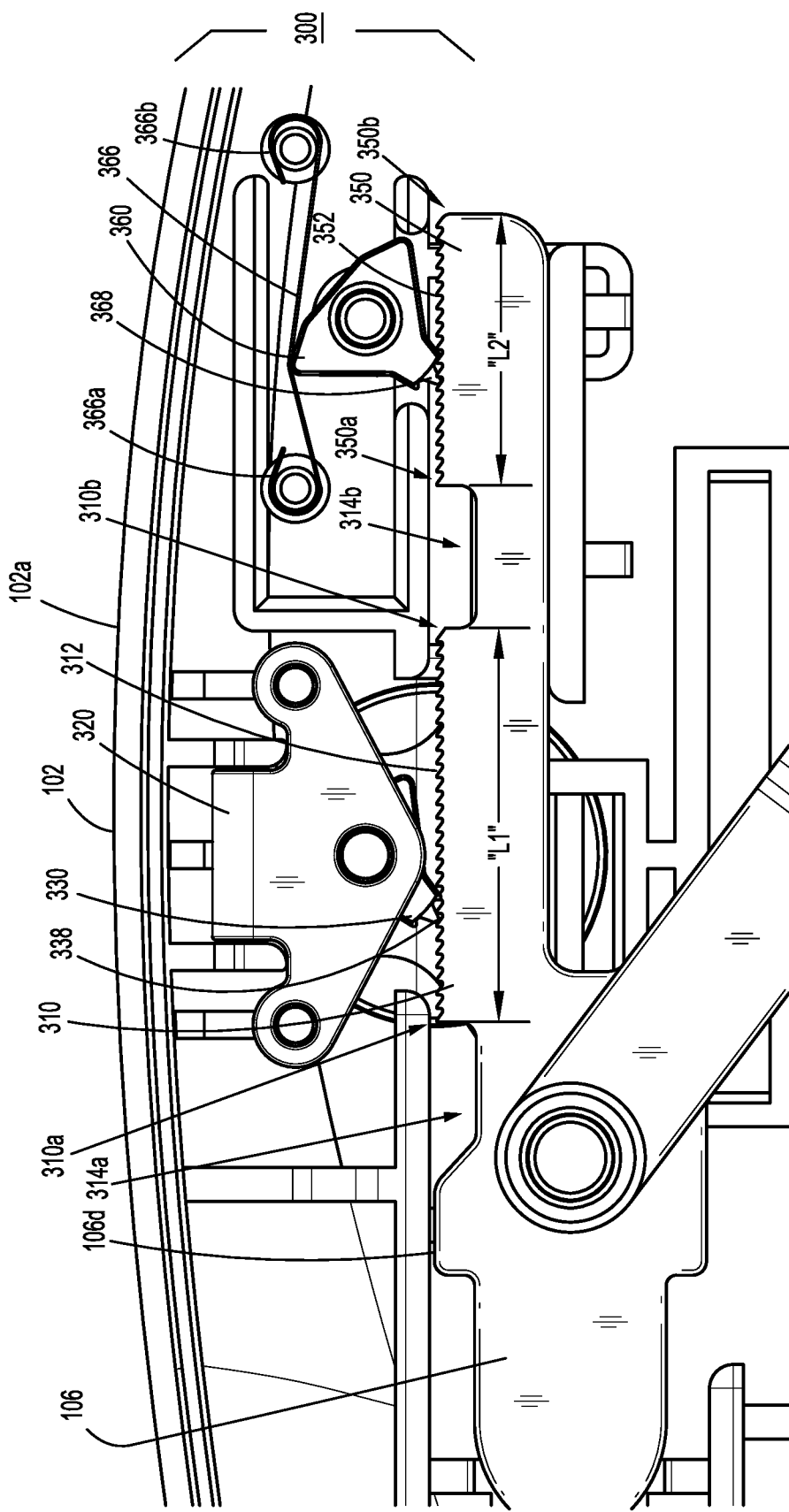
FIG. 5A is a side view, of the handle assembly of FIG. 2A, illustrating the ratchet assembly of FIG. 2B in a first configuration thereof.

With continued reference to FIG. 2B and additional reference to FIG. 5A, a normal actuation of ratchet assembly 300 is disclosed. In use, as trigger 104 is actuated, from a fully un-actuated position, the plurality of first and second rack teeth 312, 352 of the first and second racks 310, 350, respectively, are moved to a first position, into registration or engagement with first pawl tooth 338 and second pawl tooth 368 of the first and second pawls 330, 360, respectively (see FIG. 5A). It is contemplated that in the first position, first pawl spring 336 (see FIG. 3C) vertically biases first pawl 330 into operative engagement/registration with the first rack 310 and second pawl spring 366 vertically biases second pawl 360 into operative engagement/registration with the second rack 350.

First rack 310 has a first length "L1" (see FIG. 5A) which allows the first pawl 330 to reverse over the first rack 310 (from the distal well 314a; see FIG. 2B) as the first rack 310 moves in a distal direction relative to the pair of jaws 250 (see FIG. 1), as trigger 104 reaches a fully actuated position, and advance back over the first rack 310 (from the proximal end 310b of the first rack 310; not specifically shown), when the first rack 310 moves in a proximal direction relative to the pair of jaws 250, as trigger 104 reaches a fully un-actuated position. The first length "L1" of first rack 310 defines a full stroke length of trigger 104, drive bar 106 or handle assembly 100 (see FIG. 1), where a clip has been fully formed and fired from surgical clip applier 10. It is contemplated that during the full stroke length of trigger 104, in the normal actuation of ratchet assembly 300, drive bar 106 is moved a first distance relative to pawl housing 320 equal to approximately the first length "L1" of first rack 310.

Second rack 350 has a second length "L2," (see FIG. 5A) which is less than the first length "L1" of first rack 310. The second length "L2" allows the second pawl 360 to reverse over the second rack 350 (from the proximal well 314b; see FIG. 2B) as the second rack 350 moves in the distal direction relative to the pair of jaws 250 (see FIG. 1), as trigger 104 reaches a partially actuated position, and advance back over the second rack 350 (from a position that is proximal of the proximal end 350b of the second rack 350; not specifically shown), when the second rack 320 moves in a proximal direction relative to the pair of jaws 250, as trigger 104 reaches a fully un-actuated position. The second length "L2" of second rack 350 defines a partial stroke length of trigger 104, drive bar 106 or handle assembly 100 (see FIG. 1), where a clip has been partially formed, or formed enough to be fired from surgical clip applier 10 and a new clip loaded into the pair of jaws 250 without an inadvertent double loading of clips into the pair of jaws 250.

It is contemplated that in the normal actuation of ratchet assembly 300, the first and second pawls 330, 360 and the respective first and second racks 310, 350 cooperate such that the stroke length of trigger 104, drive bar 106 or handle assembly 100 is determined by the greater first length "L1" of first rack 310 to achieve a fully formed clip being fired from surgical clip applier 10.

Referring now to FIGS. 4A-5B, a partial actuation of ratchet assembly 300 is disclosed. It is contemplated that a partial actuation of ratchet assembly 300 may enable a user to fire a partially formed clip from surgical clip applier 10 when performing a cholangiogram procedure or the like. It is also contemplated that a partial actuation of ratchet assembly 300 may enable a user to abort a firing of a clip from surgical clip applier 10 if the clip is inadvertently positioned in a wrong location or if a clip is positioned over an obstruction.

In use, with reference to FIG. 5A, after trigger 104 is actuated such that, the plurality of first and second rack teeth 312, 352 of the first and second racks 310, 350, respectively, are moved to the first position, into registration or engagement with first pawl tooth 338 and second pawl tooth 368 of the first and second pawls 330, 360, respectively (see FIG. 5A), release switch 340 may be actuated towards the second position by moving or depressing first end cap 342a laterally towards the first side 328a of the pawl housing 320 such that, first extension 343a of first end cap 343a engages first side 328a of pawl housing 320 to transversely move pawl housing 320 towards second biasing member 346 and first pawl 330 out of operative engagement/registration with the plurality of first rack teeth 312 of first rack 310. The transverse movement of pawl housing 320 towards second biasing member 346, compresses second biasing member 346 between second side 328b of pawl housing 320 and internal wall 107b of second switch slot 107. In this manner, the first pawl 330 is moved transversely to a second position, out of registration or engagement with the plurality of first rack teeth 312 of the first rack 310.

In the second position, when first pawl 330 is moved transversely out of operative engagement/registration with the plurality of first rack teeth 312 and abuts a side of first rack 310, the combined biases of first pawl spring 336 and second biasing member 346 act on first pawl 330 such that first pawl 330 is wedged or held against the side of first rack 310 (see FIG. 4B) and disengaged from plurality of first rack teeth 312 until first rack 310 is moved distally such that first pawl 330 is located within proximal well 314b (not specifically shown) or until first rack 310 is moved proximally such that first pawl 330 is located within distal well 314a (see FIG. 2B), as will be further detailed.

Figure 5B:
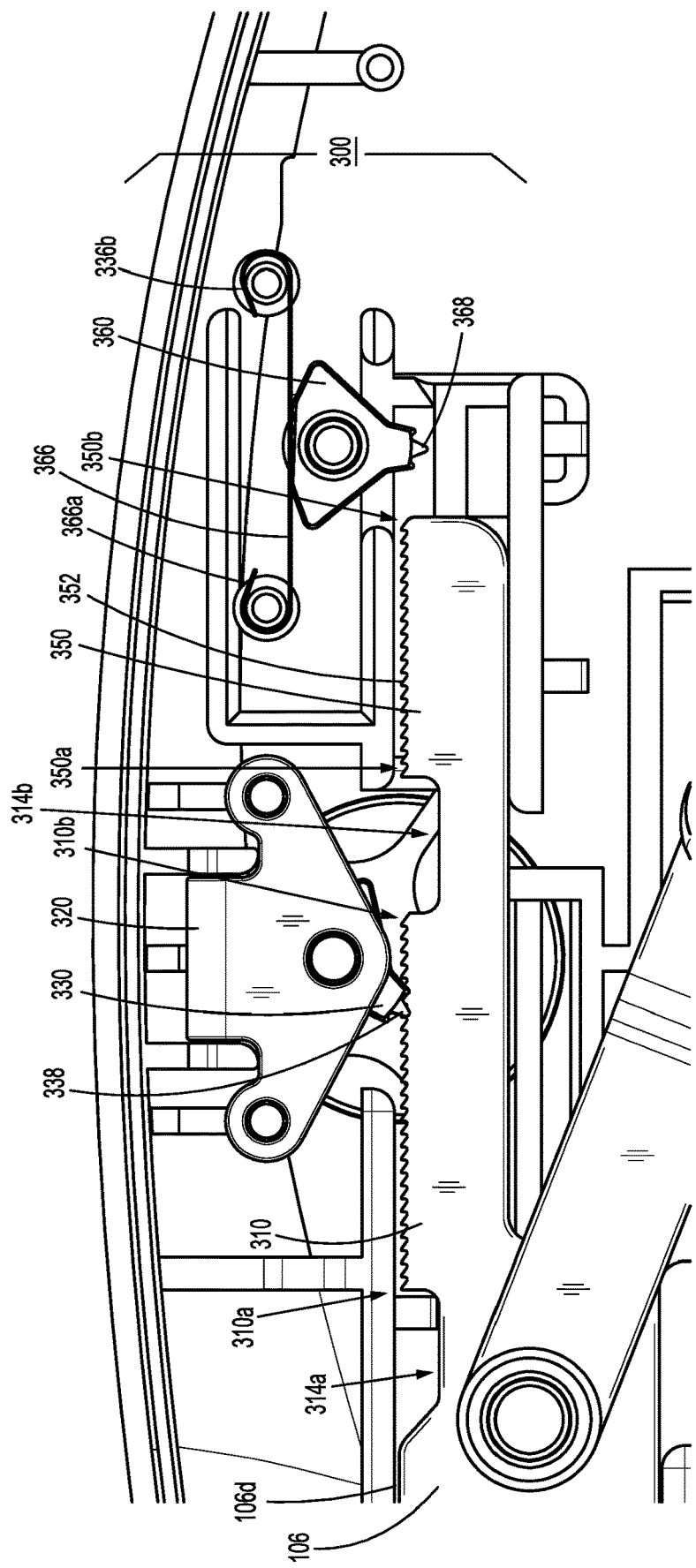
FIG. 5B is a side view, of the handle assembly of FIG. 2A, illustrating the ratchet assembly of FIG. 2B in a second configuration thereof.
Figure 6:
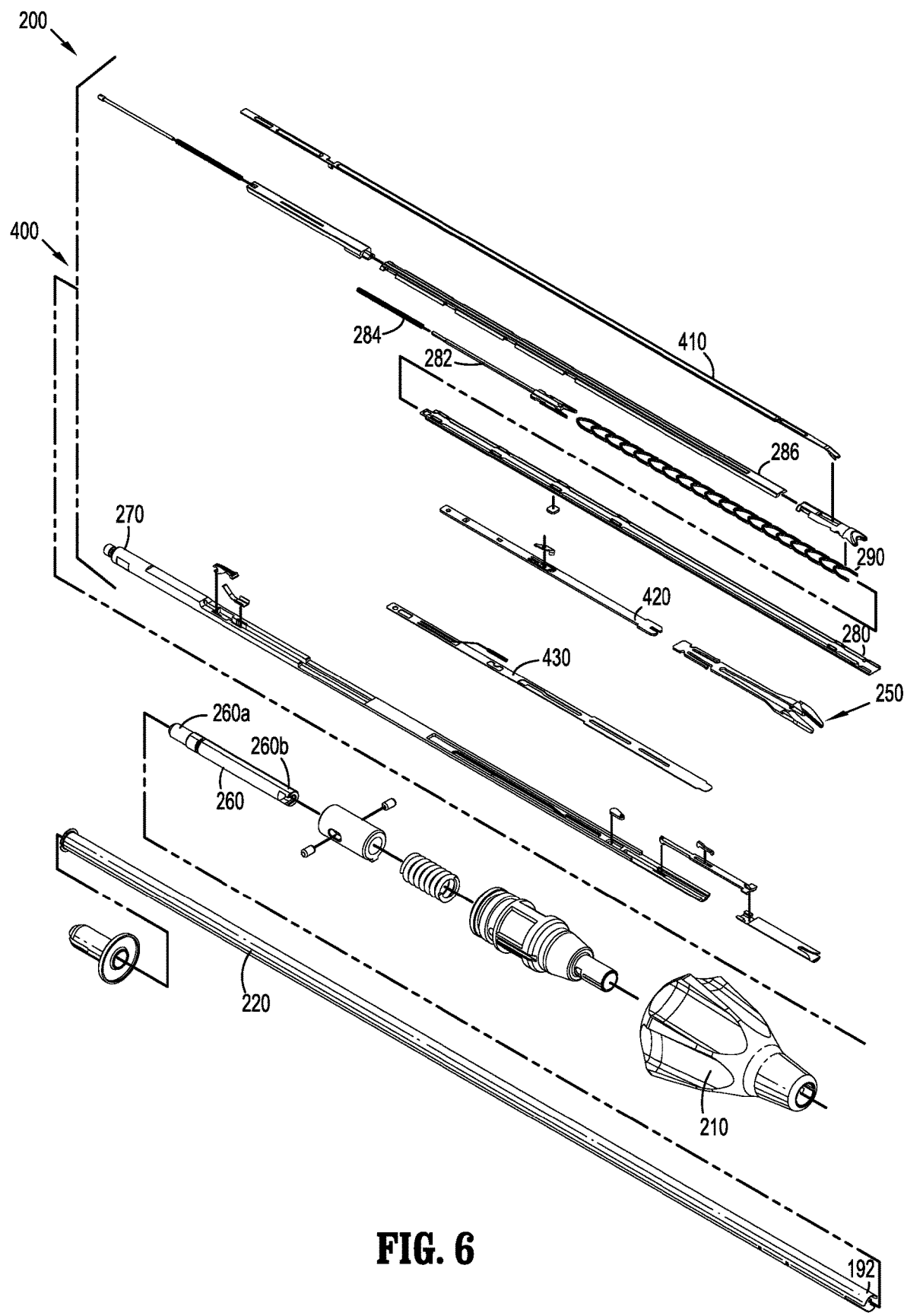
FIG. 6 is a perspective view of the endoscopic assembly of FIG. 1, with parts separated.

As shown in FIG. 4B, though release switch 340 is actuated to move the first pawl 330 to the second position, second pawl 360 remains in the first position (see FIG. 5A) until the second pawl 360 is moved to a position proximal of the proximal end 350b of the second rack 350 to clear the second rack 350, as shown in a second position of second pawl 360 in FIG. 5B. With first pawl 330 out of registration or engagement with the first rack 310 (see FIG. 4B), the stroke length of trigger 104, drive bar 106 or handle assembly 100 is determined by the lesser second length "L2" of second rack 320 (relative to first length "L1" of first rack 310). The engagement/registration between second pawl 360 and second rack 350, for a duration of the lesser second length "L2", prevents an inadvertent return of trigger 104 during a specific portion of the stroke, for example, until a clip loaded into the pair of jaws 250 is partially formed, enough to be fired from surgical clip applier 10, such that a new clip may be loaded into the pair of jaws 250 without an inadvertent double loading of clips into the pair of jaws 250. It is contemplated that during the partial stroke length of trigger 104 in the partial actuation of ratchet assembly 300, drive bar 106 is moved a second distance relative to second pawl 360 equal to approximately the second length "L2" of second rack 350.

During the return stroke, trigger 104 may be returned to a fully un-actuated position (from its partially actuated position), once second pawl 360 advances back over the second rack 350 and is disposed within the proximal well 314b to complete the partial actuation of ratchet assembly 300 (see FIG. 2B). It is contemplated that as trigger 104 is moved to the fully un-actuated position, a new clip is loaded into the pair of jaws 250.

When second pawl 360 is disposed within proximal well 314b, first pawl 330 is moved towards distal well 314a. Specifically, second biasing member 346 is permitted to expand (without being impeded by the side of first rack 310) such that second biasing force "BF2" acts on pawl housing 320 to move pawl housing 320 transversely back towards the first position wherein first pawl 330 is centered relative to first rack 310 such that first pawl 330 is engagable with the plurality of first rack teeth 312 of first rack 310 upon further longitudinal movement of first rack 310, thereby enabling or re-enabling the operability of ratchet assembly 300.

Though the figures of the present disclosure illustrate configurations where the first and second racks 310, 350 are longitudinally aligned on drive bar 106, with release switch 340 being selectively engageable with first pawl 330, it is contemplated that the first and second racks 310, 350 may include configurations where the first and second racks 310, 350 are reversed, stacked, side-by-side, or a combination thereof. Further, it is contemplated that release switch 340 may be selectively engageable with second pawl 360. In addition, it is contemplated that actuating release switch 340 may emit audible and/or tactile feedback to the user.

As noted above, and illustrated in FIG. 6, surgical clip applier 10 includes an endoscopic assembly 200 having hub assembly 210, shaft assembly 220, and the pair of jaws 250. Hub assembly 210 is rotatably mounted on nose 102c (see FIG. 2A) of housing 102 of handle assembly 100 and is connected to a proximal end portion of shaft assembly 220 to provide a three hundred sixty degree rotation of the shaft assembly 220 and the pair of jaws 250 thereon relative to a longitudinal center axis of shaft assembly 220. Hub assembly 210 has a suitable configuration so as to be rotated simply using a clinician's finger.

Endoscopic assembly 200 includes a spindle link 260 for operatively connecting drive bar 106 to a driving mechanism 400 to move the pair of jaws 250 between the spaced-apart configuration and the approximated configuration upon actuation of trigger 104. Specifically, hook member 114 (see FIG. 2B) of drive bar 106 is coupled to a first end 260a of spindle link 260 and a spindle 270 of drive mechanism 400 is coupled to a second end 260b of spindle link 260. In this manner, translation of drive bar 106 in a distal and proximal direction can thus advance and retract spindle 270, respectively.

Drive mechanism 400 further includes an elongated clip channel member 280 for retaining a number of surgical clips 290 shown in an aligned manner above the clip channel member 280. A clip follower 282 and a clip follower spring 284 are provided to urge the surgical clips 290 distally through the elongated clip channel member 280. A channel cover 286 is provided to overlay the elongated clip channel member 280 and retain and guide the clip follower 282 and clip follower spring 284 and the surgical clips 290 distally in the elongated clip channel member 280.

Drive mechanism 400 also has a feed bar 410 for feeding the surgical clips 290 between the pair of jaws 250. Drive mechanism 400 also includes a filler component 420 and a wedge plate 430.

For a more detailed description of the construction and operation of endoscopic assembly 200, reference may be made to U.S. Pat. No. 7,637,917, the entire content of which is incorporated herein by reference.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. An endoscopic surgical clip applier, comprising:
an endoscopic assembly including:
a shaft assembly; and
a pair of jaw members operatively coupled to, and extending from the shaft assembly; and
a handle assembly including:
a housing selectively connectable to the endoscopic assembly;
a fixed handle extending from the housing;
a trigger pivotally connected to the fixed handle;
a drive bar disposed within the housing of the handle assembly and operatively coupled to the trigger and the pair of jaw members to move the pair of jaw members between a spaced apart configuration and an approximated configuration upon actuation of the trigger;
a ratchet assembly disposed within the housing of the handle assembly, the ratchet assembly including:
a first rack operatively coupled to the drive bar, the first rack defining a plurality of first rack teeth;
a second rack operatively coupled to the drive bar, spaced apart from the first rack, the second rack defining a plurality of second rack teeth;
a pawl housing slidably mounted within the housing of the handle assembly, the pawl housing having a first pawl being selectively engageable with the plurality of first rack teeth of the first rack, the pawl housing being transversely slidable between a first position and a second position; and
a second pawl movably mounted within the housing of the handle assembly and being selectively engageable with the plurality of second rack teeth of the second rack,
wherein in the first position of the pawl housing, the first pawl is in registration with the plurality of first rack teeth of the first rack to prohibit reversal of a direction of movement of the trigger until the first pawl is disposed beyond a proximal end or a distal end of the first rack; and
wherein in the second position of the pawl housing, the first pawl is out of registration with the plurality of first rack teeth of the first rack to permit reversal of the direction of movement of the trigger after the second pawl is disposed distally beyond a distal end of the second rack or proximally beyond a proximal end of the second rack.

2. The endoscopic surgical clip applier according to claim 1, wherein the first rack includes a first length between the distal end and the proximal end thereof, and wherein the second rack includes a second length between the distal end and the proximal end thereof, the second length of the second rack being less than the first length of the first rack.

3. The endoscopic surgical clip applier according to claim 1, wherein the ratchet assembly includes a release switch at least partially supported within the housing of the handle assembly and operatively associated with the pawl housing, the release switch selectively actuatable to move the pawl housing from the first position thereof to the second position thereof, wherein in the second position of the pawl housing, the pawl housing is moved transversely relative to the first rack to disengage the first pawl from the plurality of first rack teeth of the first rack.

4. The endoscopic surgical clip applier according to claim 3, wherein the second pawl is selectively engageable with the plurality of second rack teeth of the second rack in a first position thereof.

5. The endoscopic surgical clip applier according to claim 3, wherein the ratchet assembly further includes a distal well disposed adjacent the distal end of the first rack, wherein the pawl housing is located in the distal well in an un-actuated position of the trigger.

6. The endoscopic surgical clip applier according to claim 4, wherein the ratchet assembly further includes a proximal well disposed between the proximal end of the first rack and the distal end of the second rack, wherein the second pawl is located in the proximal well in the un-actuated position of the trigger.

7. The endoscopic surgical clip applier according to claim 5, wherein the first rack is disposed in a position distal of the second rack.

8. The endoscopic surgical clip applier according to claim 4, wherein when the release switch is actuated, the second pawl maintains registration with the plurality of second rack teeth of the second rack, in the first position thereof, until the second pawl is disposed in the proximal well or until the second pawl is disposed proximally beyond the proximal end of the second rack.

9. The endoscopic surgical clip applier according to claim 8, wherein the drive bar is longitudinally movable upon actuation of the trigger, wherein as the drive bar is moved longitudinally in a first direction, and the release switch is not actuated, the first pawl and the second pawl are moved over the plurality of first rack teeth and the plurality of second rack teeth of the first and the second racks, respectively, such that longitudinal movement of the drive bar in a second, opposite, direction is prevented until the first pawl is disposed in the distal well and the second pawl is disposed in the proximal well or until the first pawl is disposed at the proximal end of the first rack and the second pawl is disposed proximally beyond the proximal end of the second rack.

10. The endoscopic surgical clip applier according to claim 8, wherein the drive bar is longitudinally movable upon actuation of the trigger, wherein as the drive bar is moved longitudinally in a first direction, and the release switch is actuated to move the pawl housing to the second position, longitudinal movement of the drive bar in a second, opposite, direction is prevented until the second pawl is disposed in the proximal well or until the second pawl is disposed proximally beyond the proximal end of the second rack.

11. The endoscopic surgical clip applier according to claim 10, wherein as the drive bar is moved longitudinally in the first direction, and the release switch is actuated to move the pawl housing to the second position, the second pawl is disposed beyond the proximal end of the second rack as the trigger reaches a partially actuated position, wherein the drive bar is longitudinally movable in the second, opposite, direction, as the trigger reaches a fully un-actuated position from the partially actuated position.

12. The endoscopic surgical clip applier according to claim 11, wherein the endoscopic assembly further comprises a plurality of surgical clips slidably disposed within the shaft assembly and selectively formable between the pair of jaw members, wherein when the pawl housing is in the first position, the first pawl is in registration with the first rack disposed on the drive bar such that upon actuation of the trigger, the trigger is prevented from reversing the direction of movement thereof until the trigger is moved to a fully actuated position and a distal most surgical clip of the plurality of surgical clips is fully formed between the pair of jaw members.

13. The endoscopic surgical clip applier according to claim 12, wherein when the pawl housing is in the second position, the first pawl is out of registration with the first rack disposed on the drive bar such that when the second pawl is disposed beyond the proximal end of the second rack and the trigger is moved to the partially actuated position, the trigger is capable of reversing the direction of movement thereof such that the distal most surgical clip of the plurality of surgical clips is partially formed between the pair of jaw members.

14. The endoscopic surgical clip applier according to claim 3, wherein the pawl housing defines a channel therein, and wherein the first pawl is located within the channel of the pawl housing.

15. The endoscopic surgical clip applier according to claim 14, wherein the ratchet assembly includes a switch pin, wherein the pawl housing defines a central slot therein configured to locate the switch pin, the switch pin slidably extending through the channel of the pawl housing and the first pawl to support the first pawl within the channel of the pawl housing.

16. The endoscopic surgical clip applier according to claim 15, wherein the release switch includes a first end cap and a second end cap, wherein a first side of the housing includes a first switch slot configured to slidably receive the first end cap of the release switch and a second side of the housing includes a second switch slot configured to slidably receive the second end cap of the release switch.

17. The endoscopic surgical clip applier according to claim 16, wherein the first end cap of the release switch is supported on a first end of the switch pin, on a first side of the pawl housing, and the second end cap of the release switch is supported on a second end of the switch pin, on a second, opposite side of the pawl housing, such that the release switch is accessible via the first and second end caps from the first and second sides of the pawl housing, respectively, to actuate the release switch.

18. The endoscopic surgical clip applier according to claim 3, wherein the ratchet assembly further includes a first pawl spring and a second pawl spring supported within the housing of the handle assembly, the first pawl spring being configured to bias the first pawl into engagement with the plurality of first rack teeth of the first rack and the second pawl spring being configured to bias the second pawl into engagement with the plurality of second rack teeth of the second rack.

19. An endoscopic surgical clip applier, comprising:
an endoscopic assembly including:
a shaft assembly; and
a pair of jaw members operatively coupled to, and extending from the shaft assembly; and
a handle assembly including:
a housing selectively connectable to the endoscopic assembly;
a fixed handle extending from the housing;
a trigger pivotally connected to the fixed handle;
a drive bar disposed within the housing of the handle assembly and operatively coupled to the trigger and the pair of jaw members, wherein the drive bar is longitudinally movable to move the pair of jaw members between a spaced apart configuration and an approximated configuration upon actuation of the trigger; and
a ratchet assembly disposed within the housing of the handle assembly, the ratchet assembly including:
a first rack defined on a top portion of the drive bar, the first rack including a first length between a distal end and a proximal end thereof;
a second rack defined on the top portion of the drive bar, the second rack including a second length between a distal end and a proximal end thereof, the second length of the second rack being less than the first length of the first rack;
a first pawl movable mounted within the handle assembly and being selectively engageable with the first rack, the first pawl being transversely slidable between a first position and a second position; and
a release switch at least partially supported within the housing of the handle assembly and operatively associated with the first pawl, the release switch selectively actuatable to transversely move the first pawl from the first position thereof to the second position thereof, wherein in the first position of the first pawl, the first pawl is in registration with the first rack to prohibit reversal of a direction of movement of the trigger until the drive bar is moved a first distance equal to the first length of the first rack, and wherein in the second position of the first pawl, the first pawl is moved transversely relative to the first rack to disengage the first pawl from the first rack such that, reversal of the direction of movement of the trigger is prohibited until the drive bar is moved a second distance equal to the second length of the second rack.

20. The endoscopic surgical clip applier according to claim 19, wherein the ratchet assembly includes a second pawl movable mounted within the handle assembly and being selectively engageable with the second rack, wherein upon movement of the trigger, reversal of the direction of movement of the trigger is prohibited until the second pawl is disposed distally beyond the distal end of the second rack or proximally beyond the proximal end of the second rack.

* * * * *